(12) United States Patent
Fonters et al.

(10) Patent No.: US 11,382,846 B2
(45) Date of Patent: Jul. 12, 2022

(54) DESENSITIZING ORAL CARE COMPOSITIONS AND METHODS FOR THE SAME

(71) Applicant: GABA International Holding GmbH, Therwil (CH)

(72) Inventors: Jessie Fonters, Lossy (CH); Jeannine Loetscher, Ettingen (CH); Andre Brunella, Dornach (CH)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/954,818

(22) PCT Filed: Dec. 18, 2017

(86) PCT No.: PCT/EP2017/083245
§ 371 (c)(1),
(2) Date: Jun. 17, 2020

(87) PCT Pub. No.: WO2019/120467
PCT Pub. Date: Jun. 27, 2019

(65) Prior Publication Data
US 2021/0085576 A1 Mar. 25, 2021

(51) Int. Cl.
*A61K 8/25* (2006.01)
*A61K 8/02* (2006.01)
*A61K 8/73* (2006.01)
*A61Q 11/00* (2006.01)

(52) U.S. Cl.
CPC .............. *A61K 8/25* (2013.01); *A61K 8/0245* (2013.01); *A61K 8/731* (2013.01); *A61Q 11/00* (2013.01); *A61K 2800/28* (2013.01)

(58) Field of Classification Search
CPC . A23G 4/06; A23G 4/10; A61Q 11/00; A61K 7/16

USPC .................................................. 424/10.1, 49
IPC ....................................................... A61K 7/16
See application file for complete search history.

(56) References Cited

U.S. PATENT DOCUMENTS

| | | | |
|---|---|---|---|
| 6,479,036 B1 * | 11/2002 | Stanier | A61K 8/25 106/272 |
| 8,221,726 B2 | 7/2012 | Deckner et al. | |
| 8,795,637 B2 | 8/2014 | Deckner et al. | |
| 2007/0154413 A1 | 7/2007 | Phillips et al. | |
| 2008/0268001 A1 | 10/2008 | Zaidel et al. | |
| 2009/0186090 A1 | 7/2009 | Zaidel et al. | |
| 2009/0202452 A1 | 8/2009 | Robinson et al. | |
| 2010/0047742 A1 | 2/2010 | Pitcock, Jr. et al. | |
| 2014/0377188 A1 | 12/2014 | Strand et al. | |
| 2016/0213023 A1 * | 7/2016 | Ortiz De Zarate | A23G 4/10 |

FOREIGN PATENT DOCUMENTS

WO 2009/099450 8/2009

OTHER PUBLICATIONS

Andera Gallo, "Silice Amorfa Tixosil 331." www.andreagallo.it; published Jan. 28, 2014. (Year: 2014).*
International Search Report and Written Opinion of the International Searching Authority in International Application No. PCT/EP2017/083245, dated Feb. 19, 2018.

* cited by examiner

*Primary Examiner* — Walter E Webb

(57) ABSTRACT

Oral care compositions and methods for reducing dental sensitivity or at least partially occluding dentin tubules of teeth in a subject are described herein. The oral care compositions may include an orally acceptable vehicle and a silica blocking agent configured to at least partially occlude dentin tubules of teeth. The silica blocking agents may include silica particles having a particle size distribution (D95) less than or equal to 7 μm and a BET surface area of greater than or equal to 150 m²/g.

13 Claims, No Drawings

DESENSITIZING ORAL CARE COMPOSITIONS AND METHODS FOR THE SAME

CROSS REFERENCE TO RELATED APPLICATIONS

This application is a United States Application under 35 C.F.R. 371 claiming benefit of PCT Application No. PCT/EP2017/083245, filed on Dec. 18, 2017.

BACKGROUND

Recessed gum lines expose abradable surfaces of teeth, such as cementum, to erosion. The erosion of the abradable surfaces of the teeth often leads to the exposure of dentin tubules; and thus, increased sensitivity of the teeth and/or dentin hypersensitivity. For example, the exposure of the dentin tubules consequently exposes nerves within the teeth, thereby increasing the sensitivity of the teeth to external stimuli (e.g., temperature, pressure, etc.).

In view of the foregoing, conventional oral care products or compositions thereof may often incorporate filling or blocking agents to ameliorate the sensitivity of the teeth. For example, conventional oral care compositions may incorporate filling or blocking agents to physically block or fill the dentin tubules, thereby shielding the nerve from the external stimuli. While the blocking agents have proven to be effective in reducing sensitivity, the blocking agents may often require additional components or ingredients to increase the efficacy thereof. For example, conventional oral care compositions incorporating the blocking agents also incorporate additional adhesive materials to aid or facilitate the adhesion of the blocking agents on surfaces of the teeth and/or within the dentin tubules. The additional adhesive materials, however, increase costs and the chance of incompatibility or reactivity with other components of the oral care compositions.

What is needed, then, are improved desensitizing oral care compositions without additional adhesion or adhesive materials, and methods for reducing dental sensitivity and/or dentin hypersensitivity.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition including an orally acceptable vehicle and a silica blocking agent. The silica blocking agent may include silica particles having a particle size distribution (D95) less than or equal to 7 µm and a BET surface area of greater than or equal to 150 m²/g. The silica blocking agents may be configured to at least partially occlude dentin tubules of teeth.

In at least one implementation, the oral care composition may be free of any adherent materials capable of facilitating the occlusion of the dentin tubules of the teeth, preferably the oral care composition is free of any ionic adherent materials capable of facilitating the occlusion of the dentin tubules of the teeth.

In another implementation, the silica particles may have a BET surface area of greater than or equal to 175 m²/g, greater than or equal to 200 m²/g, or greater than or equal to 250 m²/g.

In another implementation, the silica particles may have an oil absorption of greater than or equal to about 200 mL/100 g, about 240 mL/100 g, or about 250 mL/100 g.

In another implementation, the silica particles may have an average particle size of from about 3 µm to about 5 µm or about 3 µm to about 4 µm.

In another implementation, the silica blocking agent may be present in an amount of from about 2 weight % to about 10 weight %, about 4 weight % to about 6 weight %, about 4.5 weight % to about 5.5 weight %, about 4.8 weight % to about 5.2 weight %, or about 5.0 weight %, based on a total weight of the oral care composition.

In another implementation, the oral care composition may further include a silica abrasive.

In another implementation, the oral care composition may further include a silica thickener.

In another implementation, a total amount of the silica abrasive and the silica thickener present in the oral care composition may be from about 1 weight % to about 15 weight %, about 4 weight % to about 8 weight %, about 10 weight % to about 12 weight %, or about 10.5 weight % to about 11.5 weight %, based on a total weight of the oral care composition.

In another implementation, the silica blocking agent may be or include TIXOSIL® 331.

In another implementation, the oral care composition may include a hydroxyethyl cellulose.

In another implementation, the hydroxyethyl cellulose is present in an amount of from about 1.9 weight % to about 2.7 weight %, about 2.1 weight % to about 2.5 weight %, or about 2.3 weight %.

In another implementation, the oral care composition is a toothpaste.

The foregoing and/or other aspects and utilities embodied in the present disclosure may also be achieved by providing a method for reducing dental sensitivity of a subject, including contacting any one or more of the oral care compositions disclosed herein to teeth of the subject in need thereof.

The foregoing and/or other aspects and utilities embodied in the present disclosure may be achieved by providing a method for at least partially occluding dentin tubules of teeth in a subject, including contacting any one or more of the oral care compositions disclosed herein to teeth of the subject in need thereof.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

The present inventors have surprisingly and unexpectedly discovered that oral care compositions including silica particles having relatively high or greater porosity exhibit an increased flow reduction in teeth of the dentin tubules thereof, as measured by hydraulic conductance (HC), as compared to silica particles having a similar size, but relatively less porosity. Accordingly, the present inventors have surprisingly and unexpectedly discovered that oral care compositions incorporating the porous silica particles having relatively high or greater porosity exhibit relatively increased efficacy for reducing dental sensitivity. The present inventors have also surprisingly and unexpectedly discovered that the porous silica particles having relatively high or greater porosity may at least partially occlude dentin tubules to reduce dental sensitivity without the aid of any adherent materials. The present inventors have further surprisingly and unexpectedly discovered that increasing the amount of the silica particles having relatively high or greater porosity in the oral care compositions does not correspondingly increase the flow reduction, and thus, the efficacy for reducing dental sensitivity.

Compositions disclosed herein may be or include oral care compositions including a blocking agent capable of or configured to reduce tooth or dental sensitivity of human or animal subjects. Particularly, the compositions disclosed herein may be or include oral care compositions including a silica blocking agent capable of or configured to at least partially occlude dentin tubules of the human or animal subjects to thereby reduce dental sensitivity of the human or animal subjects. In a preferred implementation, the silica blocking agent may at least partially occlude dentin tubules without any adherent materials. For example, the oral care composition may include the blocking agent and be free or substantially free of any adherent materials. In a more preferred implementation, the silica blocking agent may at least partially occlude dentin tubules without any ionic adherent materials or ionic polymers utilized as adherent materials. For example, the oral care composition may include the blocking agent and be free or substantially free of any ionic adherent materials or ionic polymers utilized as adherent materials.

As discussed above, the silica blocking agents may be capable of or configured to at least partially occlude the dentin tubules. For example, the silica blocking agents may be or include silica particles sized and/or shaped to at least partially block the dentin tubules. In at least one implementation, the silica blocking agents or the silica particles thereof may have an average particle size of less than or equal to a dentin tubule. For example, the silica particles may have an average particle such that the particles may be embedded, lodged, or otherwise disposed within the dentin tubules to thereby reduce the perceived sensitivity of the teeth. In another implementation, the silica particles may have an average particle size of greater than or equal to 1 μm and/or less than or equal to 10 μm. For example, the silica particles of the silica blocking agent may have an average particle size of less than or equal to 10 μm, less than or equal to 9 μm, less than or equal to 8 μm, less than or equal to 7 μm, less than or equal to 6 μm, less than or equal to 5 μm, less than or equal to 4 μm, less than or equal to 3 μm, or less than or equal to 2 μm. In another example, the silica particles of the silica blocking agent may have an average particle size of from about 1 μm, about 2 μm, about 3 μm, or about 4 μm to about 5 μm, about 6 μm, about 7 μm, about 8 μm, about 9 μm, or about 10 μm. In yet another example, the silica particles of the silica blocking agent may have an average particle size of from about 1 μm to about 8 μm, about 2 μm to about 7 μm, about 3 μm to about 6 μm, about 3 μm to about 5 μm, or about 3 μm to about 4 μm. In a preferred implementation, the silica particles of the silica blocking agents have an average particle size of about 3.5 μm±0.2 μm, ±0.4 μm, ±0.6 μm, or ±0.8 μm.

The silica blocking agents may be present in the oral care composition in an amount of from about 1 weight % to about 10 weight %. For example, the silica blocking agents may be present in the oral care composition in an amount of from about 1 weight %, about 2 weight %, about 3 weight %, about 4 weight %, or about 5 weight % to about 6 weight %, about 7 weight %, about 8 weight %, about 9 weight %, or about 10 weight %. In another example, the silica blocking agents may be present in the oral care composition in an amount of from about 1 weight % to about 10 weight %, about 2 weight % to about 9 weight %, about 3 weight % to about 8 weight %, about 4 weight % to about 7 weight %, or about 5 weight % to about 6 weight %. In a preferred implementation, the silica blocking agents may be present in the oral care composition in an amount of from about 4 weight % to about 6 weight %, about 4.5 weight % to about 5.5 weight %, about 4.8 weight % to about 5.2 weight %, or more preferably about 5.0 weight %.

The silica blocking agent may include any type of silica particles, such as precipitated silica and/or silica gels. In a preferred implementation, the silica particles are porous. For example, the silica particles of the silica blocking agent may have a porosity greater than any one or more of the SORBOSIL® Specialty Silica, such as SORBOSIL® AC43, which are commercially available from PQ Corp. of Malvern, Pa. For example, the silica particles may have an oil absorption greater than SORBOSIL® AC43. SORBOSIL® AC43 has an oil absorption, a measure of porosity, of from about 50 ml/100 g to about 80 mL/100 g, or about 75 mL/100 g.

The silica particles of the silica blocking agents may have oil absorption (ASTM D281-12) greater than about 80 mL/100 g. For example, silica particles of the silica blocking agents may have an oil absorption greater than about 80 mL/100 g, greater than about 100 mL/100 g, greater than about 120 mL/100 g, greater than about 140 mL/100 g, greater than about 160 mL/100 g, greater than about 180 mL/100 g, greater than about 200 mL/100 g, greater than about 220 mL/100 g, greater than about 230 mL/100 g, greater than about 240 mL/100 g, greater than about 245 mL/100 g, greater than about 250 mL/100 g, greater than about 260 mL/100 g, greater than about 270 mL/100 g, greater than about 280 mL/100 g, greater than about 290 mL/100 g, greater than about 300 mL/100 g, greater than about 310 mL/100 g, greater than about 320 mL/100 g, greater than about 330 mL/100 g, greater than about 340 mL/100 g, greater than about 350 mL/100 g, or greater than about 360 mL/100 g. The silica particles of the silica blocking agents may also have oil absorption greater than about 80 mL/100 g to less than about 400 mL/100 g. In a preferred implementation, the silica particles of the silica blocking agents may also have an oil absorption greater than or equal to about 245 mL/100 g when measured with the DOA method (ISO 19246:2016) or greater than or equal to 340 mL/100 g when measured with the ASTM D281-12 method (Linseed Oil method).

The silica particles of the silica blocking agents may have a particle size distribution (D95) of from less than or equal to 8 μm and a surface area (BET surface area) of from about 150 m$^2$/g to about 250 m$^2$/g. For example, the silica particles of the silica blocking agents may have a surface area of from about 150 m$^2$/g to about 250 m$^2$/g, and a particle size distribution (D95) of from less than or equal to 8 μm, less than or equal to 7.8 μm, less than or equal to 7.6 μm, less than or equal to 7.4 μm, less than or equal to 7.2 μm, less than or equal to 7 μm, less than or equal to 6.8 μm, less than or equal to 6.6 μm, less than or equal to 6.4 μm, less than or equal to 6.2 μm, less than or equal to 6.0 μm, less than or equal to 5.8 μm, less than or equal to 5.6 μm, less than or equal to 5.4 μm, less than or equal to 5.2 μm, or less than or equal to 5 μm. In another example, the silica particles of the silica blocking agents may have a particle size distribution (D95) of from less than or equal to 7 μm, and a surface area of from about 150 m$^2$/g, about 160 m$^2$/g, about 170 m$^2$/g, about 180 m$^2$/g, about 190 m$^2$/g, or about 200 m$^2$/g to about 210 m$^2$/g, about 220 m$^2$/g, about 230 m$^2$/g, about 240 m$^2$/g, about 250 m$^2$/g, or greater. In the context of the present invention, a particle size distribution, e.g., D95 can e.g., be determined by using a volumetric dynamic laser light scattering method, preferably by using an instrument of Malvern Instruments, Ltd., Malvern, UK, preferably a Mastersizer 2000. Furthermore, in the context of the present invention, BET surface area measurements can e.g., be performed in accordance with ISO 9277:2010(E) standard with nitrogen and e.g., static volumetric and multipoint methods.

The silica particles may have a bulk density (g/cm$^3$) of from about 0.02 to about 0.10. For example, the silica particles may have a bulk density of from about 0.2, about 0.3, about 0.4, about 0.5, about 0.6 to about 0.7, about 0.8, about 0.9, or about 0.10. In a preferred implementation, the silica particles may have a bulk density of about 0.06, optionally about 0.05 to about 0.07.

The silica particles may have a BET specific surface area of greater than or equal to 150 m$^2$/g, greater than or equal to 160 m$^2$/g, greater than or equal to 170 m$^2$/g, greater than or equal to 180 m$^2$/g, greater than or equal to 190 m$^2$/g, greater than or equal to 200 m$^2$/g, greater than or equal to 210 m$^2$/g, greater than or equal to 220 m$^2$/g, greater than or equal to 230 m$^2$/g, greater than or equal to 240 m$^2$/g, greater than or equal to 250 m$^2$/g, greater than or equal to 260 m$^2$/g, greater than or equal to 270 m$^2$/g, greater than or equal to 280 m$^2$/g, greater than or equal to 290 m$^2$/g, or greater than or equal to 300 m$^2$/g.

The silica particles may have an ignition loss or loss of ignition (%)—1000° C. of greater than or equal to 1 and/or less than or equal to 25. For example, the silica particles may have a loss of ignition of less than or equal to 25, less than or equal to 24.5, less than or equal to 24, less than or equal to 23.5, less than or equal to 23, less than or equal to 22.5, less than or equal to 22, less than or equal to 21.5, less than or equal to 21, less than or equal to 20.5, less than or equal to 20, less than or equal to 19.5, or less than or equal to 19. In at least one preferred implementation, the silica particles may have a loss of ignition of from about 1 to about 25, about 15 to about 25, or about 25. In another preferred implementation, the silica particles may have a loss of ignition of less than 10.5.

The silica particles may have a pH 5 g/95 g water suspension of greater than or equal to 6.5 and less than or equal to 7.5. For example, the silica particles may have a pH 5 g/95 g water suspension of about 7±0.1, ±0.2, ±0.3, ±0.4, or ±0.5.

The silica particles may have a loss on drying or a humidity (%) 2 h at 105° C. of greater than or equal to 4 and/or less than or equal to 9. For example, the silica particles may have a humidity (%) 2 h at 105° C. of less than or equal to 8.8, less than or equal to 8.6, less than or equal to 8.4, less than or equal to 8.2, less than or equal to 8.0, less than or equal to 7.8, less than or equal to 7.6, less than or equal to 7.4, less than or equal to 7.2, or less than or equal to 7.0. In at least one preferred implementation, the silica particles may have a humidity (%) 2 h at 105° C. of less than or equal to 8. In another example, the silica particles may have a humidity (%) 2 h at 105° C. of greater than or equal to 4 and/or less than or equal to 5, greater than or equal to 4.2 and/or less than or equal to 4.8, or greater than or equal to 4.4 and/or less than or equal to 4.6.

In a preferred implementation, the silica particles include TIXOSIL® 331, which is commercially available from Solvay of Bruxelles, Belgium. In another preferred implementation, the silica particles include TIXOSIL® 365, which is also commercially available from Solvay of Bruxelles, Belgium. In yet another implementation, the silica particles include TIXOSIL® 331 and TIXOSIL® 365.

The oral care composition may be free or substantially free of any one or more adherent materials, ionic adherent materials, and/or ionic polymers utilized as adherent materials. As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

The one or more adherent materials, ionic adherent materials, and/or ionic polymers utilized as adherent materials that may be excluded may include any known or to be developed adherent materials in the art configured to attach to surfaces of an oral cavity or the teeth thereof, and/or heterogeneous biofilms present on the surfaces of the oral cavity or the teeth thereof. Particularly, the one or more adherent materials, ionic adherent materials, and/or ionic polymers utilized as adherent materials that may be excluded may include those that aid or facilitate the adhesion or interaction of the silica blocking agents to surfaces of the oral cavity, such as the surfaces of the dental tubules. The one or more adherent materials, ionic adherent materials, and/or ionic polymers utilized as adherent materials may be or include those that attach or facilitate attachment of the silica blocking agents via ionic interactions, Van der Waals forces, hydrophobic and hydrophilic interactions, and the like, and combinations thereof. Illustrative adherent materials, ionic adherent materials, and/or ionic polymers utilized as adherent materials that may be excluded from the oral care composition may be or include, but are not limited to, chitosan, chitin, a gum or a marine colloid, and the like, and combinations thereof. The adherent materials, ionic adherent materials, and/or ionic polymers utilized as adherent materials that may be excluded from the oral care composition may also be or include, but are not limited to, any one or more polymers, such as a homopolymer or a copolymer, that adhere or facilitate the adhesion of the silica blocking agents to surfaces of the oral cavity or the teeth thereof. Illustrative polymers that may be excluded from the oral care composition may include, but are not limited to, silicone polymers, polymers including monomers of polyvinyl phosphonic acid, poly(1-phosphonopropene), sulfonic acid, poly(beta styrene phosphonic acid), alpha styrene phosphonic acid, synthetic anionic polymeric polycarboxylate, maleic anhydride, maleic acid, methyl vinyl ether, and the like, and combinations thereof. In at least one implementation, copolymers of methyl vinyl ether and maleic anhydride may also be excluded from the oral care composition. Any one or more other polymers that may be excluded from the oral care composition include those disclosed and described in U.S. Pat. Nos. 4,521,551; 4,485,090; 4,138,477; 4,138,914; and 3,956,480, the contents of which are incorporated herein by reference in their entirety to the extent consistent with the present disclosure.

The oral care composition may include one or more abrasives or polishing agents. Illustrative abrasives may include, but are not limited to, sodium bicarbonate, calcium phosphate (e.g., dicalcium phosphate dihydrate), calcium sulfate, precipitated calcium carbonate, silica (e.g., hydrated silica), iron oxide, aluminum oxide, coated alumina, perlite, and the like, and combinations thereof.

In at least one implementation, the oral care composition may include one or more silica abrasives and/or silica thickeners. The silica abrasives and/or silica thickeners may be or include, but are not limited to, silica, such as fumed silica and precipitated silica, having an average particle size greater than or equal to about 5 μm. For example, the silica abrasives may have an average particle size greater than or equal to about 5 μm, greater than or equal to about 6 μm, greater than or equal to about 7 μm, greater than or equal to about 8 μm, greater than or equal to about 9 μm, greater than or equal to about 10 μm, greater than or equal to about 11 μm, greater than or equal to about 12 μm, greater than or equal to about 13 μm, greater than or equal to about 14 μm, greater than or equal to about 15 μm, greater than or equal to about 16 μm, greater than or equal to about 17 μm, greater than or equal to about 18 μm, greater than or equal to about 19 μm, greater than or equal to about 20 μm, greater than or equal to about 21 μm, greater than or equal to about 22 μm, greater than or equal to about 23 μm, greater than or equal to about 24 μm, or greater than or equal to about 25 μm.

The silica abrasives and/or silica thickeners may have a particle size distribution (D95) to greater than or equal to 6 μm. For example, the particle size distribution (D95) of the silica abrasives and/or silica thickeners may be greater than or equal to 6 μm, greater than or equal to 6.5 μm, greater than or equal to 7 μm, greater than or equal to 7.5 μm, greater than or equal to 8 μm, greater than or equal to 8.5 μm, greater than or equal to 9 μm, greater than or equal to 9.5 μm, greater than or equal to 10 μm, or greater.

The silica abrasives and/or silica thickeners may also be or include, but are not limited to, silicas having a BET specific surface area of less than or equal to 250 $m^2/g$, less than or equal to 240 $m^2/g$, less than or equal to 230 $m^2/g$, less than or equal to 220 $m^2/g$, less than or equal to 210 $m^2/g$, less than or equal to 200 $m^2/g$, less than or equal to 190 $m^2/g$, less than or equal to 180 $m^2/g$, less than or equal to 170 $m^2/g$, less than or equal to 160 $m^2/g$, less than or equal to 150 $m^2/g$, less than or equal to 140 $m^2/g$, less than or equal to 130 $m^2/g$, less than or equal to 120 $m^2/g$, less than or equal to 110 $m^2/g$, less than or equal to 100 $m^2/g$, less than or equal to 90 $m^2/g$, less than or equal to 80 $m^2/g$, less than or equal to 70 $m^2/g$, less than or equal to 65 $m^2/g$, less than or equal to 60 $m^2/g$, less than or equal to 55 $m^2/g$, or less than or equal to 50 $m^2/g$. Illustrative silica abrasives and/or silica thickeners may be or include, but are not limited to, those designed under the trade name ZEODENT®, which are commercially available from J.M. Huber Corp., precipitated silica, such as silica xerogels, which are disclosed and described in U.S. Pat. Nos. 3,538,230 and 3,862,307, the contents of which are incorporated herein by reference to the extent consistent with the present disclosure, SYLOID®, which is commercially available from Grace Corporation of Colombia, Md., and those disclosed and described in U.S. Pat. No. 4,340,583, which is hereby incorporated by reference to the extent consistent with the present disclosure. In at least one implementation, the silica abrasives may include the SORBOSIL® Specialty Silicas, such as SORBOSIL® AC43, which are commercially available from PQ Corp. of Malvern, Pa. In a preferred implementation, the silica abrasives include TIXOSIL® 63, which is commercially available from Solvay of Bruxelles, Belgium and SIDENT® 8, which is commercially available from Evonik Industries AG of Essen, Germany.

The amount of any one or more of the silica abrasives and/or silica thickeners present in the oral care composition may vary widely. In at least one implementation, a total amount of the silica abrasives and/or silica thickeners present in the oral care composition may be from about 6 weight % to about 25 weight %, based on a total weight of the oral care composition. For example, the total amount of the silica abrasives and silica thickeners present in the oral care composition may be from about 5 weight %, about 6 weight %, about 7 weight %, about 8 weight %, about 9 weight %, about 10 weight %, or about 10.5 weight % to about 11.5 weight %, about 12 weight %, about 13 weight %, about 14 weight %, about 15 weight %, about 16 weight %, about 17 weight %, about 18 weight %, about 19 weight %, about 20 weight %, about 21 weight %, about 22 weight %, about 23 weight %, about 24 weight %, or about 25 weight %, based on a total weight of the oral care composition. In another example, the total amount of the silica abrasives and silica thickeners present in the oral care composition may be from about 5 weight % to about 17 weight %, about 6 weight % to about 16 weight %, about 7 weight % to about 15 weight %, about 8 weight % to about 14 weight %, about 9 weight % to about 13 weight %, about 10 weight % to about 12 weight %, or about 10.5 weight % to about 11.5 weight %. In another example, the total amount of the silica abrasives and silica thickeners present in the oral care composition may be from about 5 weight % to about 25 weight %, about 6 weight % to about 24 weight %, about 7 weight % to about 23 weight %, about 8 weight % to about 22 weight %, about 9 weight % to about 21 weight %, about 10 weight % to about 20 weight %, or about 10.5 weight % to about 19 weight %. In a preferred implementation, the total amount of the silica abrasives and silica thickeners present in the oral care composition may be from about 10.5 weight % to about 11.5 weight %, preferably about 11 weight %. In an exemplary implementation, the silica abrasives and silica thickeners include TIXOSIL® 63 and SIDENT® 8, and the silica abrasives and silica thickeners are present in an amount of from about 10.5 weight % to about 11.5 weight %, preferably about 11 weight %.

In another implementation, any one of the silica abrasives and/or silica thickeners may be present in the oral care composition in an amount of from about 1 weight % to about 15 weight %, based on a total weight of the oral care composition. For example, the amount of any one of the silica abrasives and/or silica thickeners present in the oral care composition may be from about 1 weight %, about 1.5 weight %, about 2 weight %, about 2.5 weight %, about 3 weight %, about 3.5 weight %, about 4 weight %, about 4.5 weight %, about 5 weight %, or about 5.5 weight % to about 6.5 weight %, about 7 weight %, about 7.5 weight %, about 8 weight %, about 9 weight %, about 10 weight %, about 11 weight %, about 12 weight %, about 13 weight %, about 14 weight %, or about 15 weight %, based on a total weight of the oral care composition. In another example, the amount of any one of the silica abrasives and/or silica thickeners present in the oral care composition may be from about 4 weight % to about 8 weight %, about 4.5 weight % to about 7.5 weight %, about 5 weight % to about 7 weight %, or about 5.5 weight % to about 6.5 weight %. In yet another example, the amount of any one of the silica abrasives and/or silica thickeners present in the oral care composition may be from about 1 weight % to about 15 weight %, about 2 weight % to about 14 weight %, about 3 weight % to about 13 weight %, or about 4 weight % to about 12 weight %. In an exemplary implementation, the silica abrasives and silica thickeners include TIXOSIL® 63 in an amount of from about 5.5 weight % to about 6.5 weight %, preferably about 6 weight %, and SIDENT® 8 in an amount of from about 4.5 weight % to about 5.5 weight %, preferably about 5 weight %.

The oral care composition may include one or more water soluble polymers. Illustrative water soluble polymers may include, but are not limited to, cellulose ethers, methacrylates, polyvinylpyrollidone, and the like, and combinations or mixtures thereof. For example, the water soluble polymer may include a cellulose ether, selected from one or more of hydroxyalkyl cellulose polymers, such as hydroxypropyl methyl cellulose (HPMC), hydroxypropyl cellulose, hydroxyethyl cellulose, methyl cellulose, carboxymethyl cellulose, and mixtures or combinations thereof. In a typical implementation, the water soluble polymer includes one or more hydroxyalkyl cellulose polymers. Illustrative hydroxyalkyl cellulose polymers may be or include, but are not limited to, hydroxyethyl cellulose, hydroxypropyl methyl cellulose, hydroxyethylpropyl cellulose, hydroxybutyl methyl cellulose, carboxymethyl cellulose, and the like, and mixtures or combinations thereof. In a preferred implementation, the oral care composition includes hydroxyethyl cellulose, more preferably TYLOSE® H 10000 P2, which is commercially available from Shin-Etsu, Tokyo, Japan. In at least one implementation, hydroxypropyl methyl cellulose (HPMC) is not included in the oral care composition as a water soluble polymer.

The amount of the water soluble polymers present in the oral care composition may be from about 1.0 weight % to about 3.0 weight %. For example, the amount of the water soluble polymers present in the oral care composition may be from about 1.0 weight %, about 1.2 weight %, about 1.4 weight %, about 1.6 weight %, about 1.8 weight %, about 1.9 weight %, or about 1.95 weight % to about 2.05 weight %, about 2.1 weight %, about 2.2 weight %, about 2.4 weight %, about 2.6 weight %, about 2.8 weight %, or about 3.0 weight %. In another example, the amount of the water soluble polymer present in the oral care composition may be from about 1.0 weight % to about 3.0 weight %, about 1.2 weight % to about 2.8 weight %, about 1.4 weight % to about 2.6 weight %, about 1.6 weight % to about 2.4 weight %, about 1.8 weight % to about 2.2 weight %, about 1.9 weight % to about 2.1 weight %, or about 1.95 weight % to about 2.05 weight %. In a preferred implementation, the amount of the water soluble polymers present in the oral care composition may be from about 1.9 weight % to about 2.1 weight %, preferably about 1.95 weight % to about 2.05 weight %, more preferably about 2.0 weight %. In another preferred implementation, the amount of the water soluble polymer present in the oral care composition may be about 2.3 weight %±0.01 weight %, ±0.05 weight %, ±0.08 weight %, ±±0.1 weight %, ±0.15 weight %, ±0.2 weight %, or ±0.25 weight %, based on a total weight of the oral care composition.

The oral care composition may also include one or more flavoring agents. Illustrative flavoring agents may include, but are not limited to, essential oils and various flavoring aldehydes, esters, alcohols, and the like. The flavoring agents may also include, but are not limited to, sweeteners, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, dihydrochalcones and mixtures thereof. Examples of the essential oils include oils of aniseed, spearmint, peppermint, wintergreen, sassafras, clove, sage, eucalyptus, marjoram, cinnamon, lemon, lime, grapefruit, and orange. In another example, the flavoring agents may include menthol, carvone, and anethole. The amount of the one or more flavoring agents present in the oral care composition may be from about 0.2 weight % to about 2.0 weight %.

The oral care composition may further include one or more fluoride ion sources (e.g., soluble fluoride salts). A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In a typical implementation, the fluoride ion source may provide fluoride ions in an amount of from about 200 ppm to about 2000 ppm. For example, the fluoride ion source may provide fluoride ions in an amount of from about 200 ppm, about 300 ppm, about 400 ppm, about 500 ppm, about 600 ppm, about 700 ppm, about 800 ppm, about 900 ppm, about 1,000 ppm, about 1,100 ppm, about 1,200 ppm, about 1,300 ppm, or about 1,400 ppm to about 1,500 ppm, about 1,600 ppm, about 1,700 ppm, about 1,800 ppm, about 1,900 ppm, about 2,000 ppm. In a preferred implementation the fluoride ion source may provide fluoride ions in an amount of from about 1,300 ppm to about 1,500 ppm, about 1,350 ppm to about 1,450 ppm, or about 1,400 ppm.

It should be appreciated by one having ordinary skill in the art, that the oral care composition may include other additional ingredients/components. For example, the oral care composition may include anti-caries agents, desensitizing agents, viscosity modifiers, diluents, surface active agents (e.g., emulsifiers, foam modulators, etc.), pH modifying agents (e.g., acids and bases), humectants, mouth feel agents, sweetening agents, flavor agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials.

The oral care composition may form at least a portion of or be used in any one or more oral care products that are capable of contacting the silica blocking agents thereof with the surfaces of the oral cavity or the teeth thereof. As used herein, the expression "oral care composition" may refer to a product or a composition thereof that in the ordinary course of usage is maintained in the oral cavity in an effective amount and in a time sufficient to contact at least a portion of the surfaces of the oral cavity, including the teeth and/or oral tissue, for purposes of oral activity. As used herein, the expression "effective amount," may refer to an amount of a compound or a composition sufficient to induce a positive effect or benefit and/or an amount low enough to prevent or reduce a negative effect or serious side effects. Illustrative oral care products may include, but are not limited to, a toothpaste (dentifrice), a prophylactic paste, a tooth powder, a tooth polish, a tooth gel (e.g., a whitening gel), a chewing gum, a lozenge, a mouthwash, a whitening strip, a paint-on gel, varnish, veneer, and tube, syringe or dental tray including a gel or paste, or a gel or paste coated on an application support such as dental floss or a toothbrush (e.g., a manual, electric, sound, a combination thereof or ultrasound toothbrush). In a preferred implementation, the oral care composition may form at least a portion of or be used in toothpaste. For example, the oral care composition may be a gel of the toothpaste, or a whitening gel to be combined with the toothpaste.

The oral care composition may include or be combined with an orally acceptable vehicle to form the oral care product (e.g., the toothpaste). As used herein, "orally acceptable vehicle" may refer to a suitable vehicle, ingredient, or combination of ingredients, which can be used to form and/or apply the oral care composition to the surfaces of the oral cavity in a safe and effective manner. It should be appreciated that the orally acceptable vehicle may include materials such as, but not limited to, one or more antibacterial agents, anticalculus agents, buffers, additional abrasives, sources of peroxide (e.g., hydrogen peroxide), alkali metal bicarbonate salts, thickening materials, humectants, water, surfactants, titanium dioxide, cooling agents, coloring agents, and the like, and combinations thereof. In an exemplary implementation, the orally acceptable vehicle may include at least glycerin.

All ingredients for use in the compositions described herein should be orally acceptable. As used herein, "orally acceptable" may refer to any ingredient that is present in a composition as described in an amount and form that does not render the composition unsafe for use in the oral cavity.

The present disclosure provides methods for reducing dental sensitivity of teeth in a human or animal subject in need thereof, and methods for at least partially occluding dentin tubules of teeth in the human or animal subject in need thereof. As used herein "animal subject" may include higher order non-human mammals such as canines, felines, and horses. The methods may include contacting any one or more of the oral care compositions disclosed herein with surfaces of an oral cavity. Contacting the oral care compositions with the surfaces of the oral cavity may include brushing, flossing, irrigating, wiping, rinsing (lavage of oral cavity), foam/gel and in-tray application, masticating, spraying, painting, and the like. The method may also include at least partially disposing small, porous silica particles within dentin tubules of the teeth without the aid of any adherent material.

The oral care compositions may be applied and/or contacted with the surfaces of the oral cavity or the teeth thereof at predetermined intervals. For example, the oral care compositions may be applied and/or contacted with the surfaces of the teeth on a daily basis, at least one time a day for multiple days, or alternatively every other day. The oral care compositions may be utilized for up to 2 weeks, up to 3 weeks, up to 4 weeks, up to 6 weeks, up to 8 weeks, or greater.

The following example and other implementations described herein are exemplary and not intended to be limiting in describing the full scope of compositions and methods of this disclosure. Equivalent changes, modifications and variations of specific implementations, materials, compositions and methods may also fall within the scope of the present disclosure.

EXAMPLE

The efficacy of several oral care compositions were evaluated in a clinical setting, for their ability reduce dental sensitivity. Particularly, eight separate test oral care compositions (1)-(8) were prepared by combining the ingredients/components according to Table 1, and each of the oral care compositions was evaluated via hydraulic conductance (HC) to determine their efficacy for reducing dental sensitivity. It should be appreciated that none of the test oral care compositions (1)-(8) included any adherent materials to aid or facilitate the occlusion of the dentin tubules. The general procedures for HC treatment is discussed and disclosed in Zhang, et al. *The Effects of pain free desensitizer or dentine permeability and tubule occlusion over time, in vitro*, Journal of Clinical Periodontology, (1998), the contents of which are incorporated herein by reference to the extent consistent with the present disclosure.

TABLE 1

| INGREDIENT/COMPONENT | Oral Care Compositions (1)-(8) | | | | | | | |
|---|---|---|---|---|---|---|---|---|
| | (1) | (2) | (3) | (4) | (5) | (6) | (7) | (8) |
| TIXOSIL ® 331 (wt %) | — | 5.0 | — | 6.0 | 5.0 | 7.0 | 4.0 | 5.0 |
| SORBOSIL ® AC43 (wt %) | — | — | 5.0 | — | — | — | — | — |
| TIXOSIL ® 63 (wt %) | 6.0 | 6.0 | 6.0 | 6.0 | — | — | 6.0 | 6.0 |
| S1DENT ® 8 (wt %) | 5.0 | 5.0 | 5.0 | 5.0 | 11.0 | 7.0 | 5.0 | 5.0 |
| Hydroxyethyl cellulose (wt %) | 2.5 | 2.0 | 2.0 | 2.0 | 2.15 | 2.0 | 2.2 | 2.3 |
| Pigment | 0.9 | 1.0 | 1.0 | 1.0 | 1.0 | 1.0 | 1.0 | 1.0 |
| Excipients (Water, Humectants, Surfactants, Solubilizers, Flavors, Sweeteners, Fluoride) (wt %) | 85.6 | 81.0 | 81.0 | 80.0 | 80.85 | 83.0 | 81.8 | 80.7 |
| TOTAL (wt %) | 100 | 100 | 100 | 100 | 100 | 100 | 100 | 100 |

For the HC study, human third molars were stored after extraction in a thymol/ethanol (5%) solution, disinfected in a 10% hydrogen peroxide solution for 24-48 hours, and then stored in the thymol/ethanol (5%) solution until use. At the time of use, each the human molars were used to prepare dentin disks. Particularly, each of the human molars was cut from the crown and roots with a diamond bladed saw, embedded in epoxy resin, and ground using wet grit paper to create an even and uniform surface. The dentin discs were then stored for 2 minutes (min) in 2% citric acid to etch the surface thereof, ultrasonicated for 60 seconds, and stored in a 70% ethanol solution for 24-48 hours prior to treatment under HC. Prior to treatment, each of the dentin disks were stored for 2 min in 6% citric acid, ultrasonicated for 60 sec, and subsequently stored in a phosphate buffer (PBS) at a pH of about 7 for 30 sec.

Each of the dentin disks were then treated with the respective oral care composition (1)-(8), and the fluid flow was measured via HC. The results of the HC evaluation/treatment are summarized in Table 2.

TABLE 2

Flow Reduction of Oral Care Composition (1)-(8) as Measured by Hydraulic Conductance

| Oral Care Composition | (1) | (2) | (3) | (4) | (5) | (6) | (7) | (8) |
|---|---|---|---|---|---|---|---|---|
| Median (%) | 21.2 | 70.2 | 42.8 | 59.2 | 48.1 | 47.4 | 47.5 | 70.3 |
| Mean (%) | 17.2 | 66.9 | 35.7 | 54.0 | 49.7 | 45.7 | 47.0 | 66.5 |
| Std. Dev. (%) | 31.8 | 19.8 | 26.4 | 27.6 | 23.2 | 23.2 | 28.9 | 23.0 |
| Std. Error of Mean (%) | 3.8 | 2.6 | 7.6 | 5.6 | 3.9 | 6.7 | 8.3 | 3.8 |

As indicated by Table 2, the test oral care composition (2), which included no adherent materials and 5 weight % of the small, porous silica particles (relatively high surface area), namely TIXOSIL® 331, surprisingly and unexpectedly exhibited an average/mean flow reduction better or greater than the test oral care composition (1). The flow reduction of the test oral care composition (2) demonstrated that small, porous silica particles such as TIXOSIL® 331 sufficiently occlude dentin tubules without the aid of any adherent materials. Without being bound by theory, it is believed that the relatively greater porosity of the silica particles provides increased surface area; and thus, an increased interaction or ability to interact or bond with surfaces of the dentin tubules. For example, the increased surface area of the silica particles in combination with the small particle size distribution allows for increased adhesion to surfaces of the dentin tubules and/or increased agglomeration with other silica particles. The increased adhesion or interaction to the surfaces of the dentin tubules considerably reduces respective diameters of the dentin tubules and restricts the flow therethrough. The reduction in the diameter of the dentin tubules treated with the test oral care composition (2) was confirmed via scanning electron microscopy (SEM).

As also indicated in Table 2, the test oral care composition (1) which did not include the small, porous silica particles (TIXOSIL® 331) exhibited relatively lower flow reduction. This demonstrated that the occlusion or the reduction in flow was attributed mainly to the small, porous silica particles, and not the other silica particles present, or the hydroxyethyl cellulose.

As further indicated in Table 2, the test oral care composition (2) surprisingly and unexpectedly exhibited relatively greater flow reduction as compared to test composition (3), which included SORBOSIL® AC43. It should be appreciated that SORBOSIL® AC43 has a similar particle size distribution, but exhibits relatively less porosity as compared to the TIXOSIL® 331 utilized in test oral care composition (2). Accordingly, it is surprisingly and unexpectedly discovered that flow reduction without the aid of the adherent materials is not only attributed to the size of the silica particles, but to the porosity and/or surface area of the silica particles. Particularly, the particle size distribution or size of the silica particles in combination with the porosity or surface area of the silica particles.

As further indicated in Table 2, increasing the amount of the small, porous silica particles did not correspondingly increase flow reduction. Particularly, increasing the amount of TIXOSIL® 331 from at least about 4.0 weight %, or at least about 5.0 weight %, as in test oral care composition (2) to about 6.0 weight % and 7.0 weight %, as in test oral care compositions (4) and (6), respectively, did not result in a corresponding increase in the flow reduction.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

The invention claimed is:

1. An oral care composition, comprising an orally acceptable vehicle, a silica thickener, and a silica blocking agent, wherein the silica blocking agent comprises silica particles having a particle size distribution (D95) less than or equal to 7 μm and a BET surface area of greater than or equal to 150 $m^2/g$, wherein the silica blocking agent is present in an amount sufficient to occlude a dentin tubule, wherein the oral care composition is a toothpaste.

2. The oral care composition according to claim 1, wherein the oral care composition is free of any adherent materials capable of facilitating the occlusion of the dentin tubules of the teeth.

3. The oral care composition according to claim 1, wherein the silica particles of said silica blocking agent have a BET surface area of greater than or equal to 175 $m^2/g$, greater than or equal to 200 $m^2/g$, or greater than or equal to 250 $m^2/g$.

4. The oral care composition according to claim 1, wherein the silica particles of said silica blocking agent have an oil absorption of greater than or equal to about 200 mL/100 g, about 240 mL/100 g, or about 250 mL/100 g.

5. The oral care composition according to claim 1, wherein the silica particles of said silica blocking agent have an average particle size of from about 3 μm to about 5 μm or about 3 μm to about 4 μm.

6. The oral care composition according to claim 1, wherein the silica blocking agent is present in an amount of from about 2 weight % to about 10 weight %, about 4 weight % to about 6 weight %, about 4.5 weight % to about 5.5 weight %, about 4.8 weight % to about 5.2 weight %, or about 5.0 weight %, based on a total weight of the oral care composition.

7. The oral care composition according to claim 1, further comprising a silica abrasive.

8. The oral care composition according to claim 7, wherein a total amount of the silica abrasive and the silica thickener present in the oral care composition is from about 1 weight % to about 15 weight %, about 4 weight % to about 8 weight %, about 10 weight % to about 12 weight %, or about 10.5 weight % to about 11.5 weight %, based on a total weight of the oral care composition.

9. The oral care composition according to claim 1, further comprising a hydroxyethyl cellulose.

10. The oral care composition according to claim 9, wherein the hydroxyethyl cellulose is present in an amount of from about 1.9 weight % to about 2.7 weight %, about 2.1 weight % to about 2.5 weight %, or about 2.3 weight %.

11. A method for treating, preventing, or ameliorating a symptom associated with dental sensitivity in a subject in need thereof, comprising contacting an oral cavity surface of said subject with an oral care composition according to claim 1.

12. A method for occluding a dentin tubule of a subject in need thereof, comprising contacting an oral cavity surface of said subject with an oral care composition according to claim 1.

13. The oral care composition according to claim 2, wherein the oral care composition is free of any ionic adherent materials capable of facilitating the occlusion of the dentin tubules of the teeth.

* * * * *